United States Patent [19]

Wrighton et al.

[11] Patent Number: 4,473,695
[45] Date of Patent: Sep. 25, 1984

[54] SYNTHESIS OF N,N'-DIALKYL-4'BIPYRIDINIUM REAGENTS

[75] Inventors: Mark S. Wrighton, Winchester, Mass.; Dana C. Bookbinder, East Greenwich, R.I.

[73] Assignee: Massachusetts Institute of Technology, Cambridge, Mass.

[21] Appl. No.: 319,177

[22] PCT Filed: Jul. 14, 1981

[86] PCT No.: PCT/US81/00949
§ 371 Date: Jan. 15, 1982
§ 102(e) Date: Jan. 15, 1982

[51] Int. Cl.³ .................................... C07D 213/22
[52] U.S. Cl. ............................. 546/266; 350/357

[58] Field of Search ........................................ 546/266

[56] References Cited
PUBLICATIONS

Bookbinder & Wrighton, Journal of the American Chemical Society, vol. 102, No. 15, pp. 5123-5125, Jul. 16, 1980.

Primary Examiner—Alan L. Rotman
Attorney, Agent, or Firm—Arthur A. Smith, Jr.; Thomas J. Engellenner

[57] ABSTRACT

A novel class of dialkyl and dialkyl-aromatic viologens (4,4'dipyridinium compounds) and their salts which may be polymerized and covalently bonded to electrodes for use in electronic display systems.

13 Claims, 1 Drawing Figure a
SYNTHESIS OF N,N'-DIALKYL-4'BIPYRIDINIUM REAGENTS This application is based upon and claims the priority of International Patent Application No. PCT/US81/00949 filed July 14, 1981.

TECHNICAL FIELD

The field of this invention is chemical compounds and, particularly, chemical compounds suitable for use in electrochromic systems.

BACKGROUND ART

Recently there has been considerable interest in reduction-oxidation (redox) active compounds for use in electronic displays. Such electrochromic materials are suitable for use whenever a light absorbing, rather than a light emitting, display can be employed. Electochromic materials are often preferred because of their low power consumption and their ability to operate without a constantly applied power source.

A number of compounds which change color as a result of electrochemical reactions are known. For example, polyvinylferrocene, polynitrostyrene or polymers from hydrolytically unstable ferrocene monomers have been confined to the surface of electrode materials. All of these materials are electrochromic. Polynitrostyrene, a pale yellow solid, is claimed to give an electrode a red appearance upon reduction whereas ferrocene-centered polymers turn from yellow/orange to blue upon oxidation. These results are encouraging, but the ferrocenes are too weakly colored and the reduction of polynitrostyrene is not readily reversible in the presence of moisture.

Compounds formed from 4,4'-bipyridinium, known as viologens, also exhibit electrochromic behavior. For example, dialkyl-4,4'-bipyridinium di-cations and their associated anions (dichloride, dibromide or di-iodide) form contrasting colors. These viologen di-cations range from colorless, yellow, and to red, while monocations are a striking blue-purple. Two basic problems with viologens are their long term stability as coatings and their sluggish switching speeds (rates of color change) at typical coating or solution concentrations.

There exists a need for electrochromic materials which can be immobilized, and preferably covalently bonded, upon electrode surfaces and which can be repeatedly subjected to redox actions in display systems. Moreover there is a need for electrochromic materials that can respond rapidly to an applied potential and yield a strong color (i.e. high molar absorbivity).

DISCLOSURE OF THE INVENTION

We have discovered a novel class of dialkyl and dialkyl-aromatic viologens (4,4'-bipyridinium compounds) which may be polymerized and covalently bonded, or otherwise confined, to the surfaces of electrodes. These surface confined compounds exhibit the colors of viologen dications, colorless when oxidized, purple when reduced, while having the ability to avoid dissolution into the electrolyte in their oxidized or reduced, radical cationic, state. Further the surface confined compounds can be reduced and reoxidized rapidly and without degradation.

In one embodiment, our reagents include silicon groups which provide sites for attachment to surfaces bearing OH groups and, in the presence of $H_2O$, also promote polymerization. In particular, silicon alkoxides, $Si(OR)_3$, such as $Si(OMe)_3$; $Si(OEt)_3$; $Si(OPr)_3$; $Si(OBu)_3$; and silicon halogens such as $SiCl_3$ may be used. When the silicon alkoxide reagents are applied to the OH bearing surface, the alkoxyls leave the compound and combine with hydrogen from the OH bearing surface to form alcohols while the silicon is thus free to bind to the surface oxide and also polymerize with neighboring silicon atoms. In a similar fashion silicon halogens may also be employed with the halogen being displaced to permit silicon oxide covalent bonding. The resulting coating is a polysiloxane polymeric structure with viologens as a functional group on each silicon atom. Although silicon groups are suitable binding agents other agents, such as boron dihalides and, in particular, $BCl_2$, may also be used.

We have also found that a wide range of alkyl and aromatic groups can be used to link the viologen center of our compounds to the binding groups. Alkyl chains of one or more carbon atoms as well as alkyl-aromatic combinations may be employed. The only limitation appears to be that the alkyl-linking group must be short enough to support electron charge transfer.

Our compounds have been used in a number of electrochromic display systems. The mechanism for the electrochromic behavior is as follows: The compound is coated onto an electrode which is immersed in a electrolytic solution together with a second, physically remote, electrode. A voltage is applied between the electrodes. Our compounds are reduced in two distinct and reversible, one-electron, transfer steps, first to the highly colored radical mono-cation and then to the neutral molecule.

Any polar solvent can serve as the solvent. The supporting electrolyte can be tetra alkyl ammonium halide $[R_4N]X$ in nonaqueous solvents and alkaline halides such as LiCl NaCl or KBr can be used in aqueous solvents. In acetonitrile solvent we observe $E°$ values of $-0.5 \pm 0.05$ and $-0.9V \pm 0.05$ (vs. a saturated caramel reference electrode) for the first and second reductions, respectively, for surface-confined polymer in Example I below. In other electrolytes such as propylene carbonate and methylene chloride, reversible charge transfer, spectral shifts for both reduction steps are observed. In water rapid reversible charge transfer, spectral shifts for the first reduction are observed.

In the preferred embodiment, our compounds are prepared as dication salts, with halides or other anions used to neutralize the compound. Two preferred salts are dichlorides and dibromides.

We have produced electrochromic coatings from our compounds up to 100 monomer layers thick while retaining the viologen's rapid electrochromic response (on the order of 10 milliseconds). Additionally the quality of the color exhibited has been steadfast; absorbion on the order of 90% has been observed in the visible region. These qualities have been maintained in samples tested over 20,000 redox cycles.

BEST MODES

Figure 1:
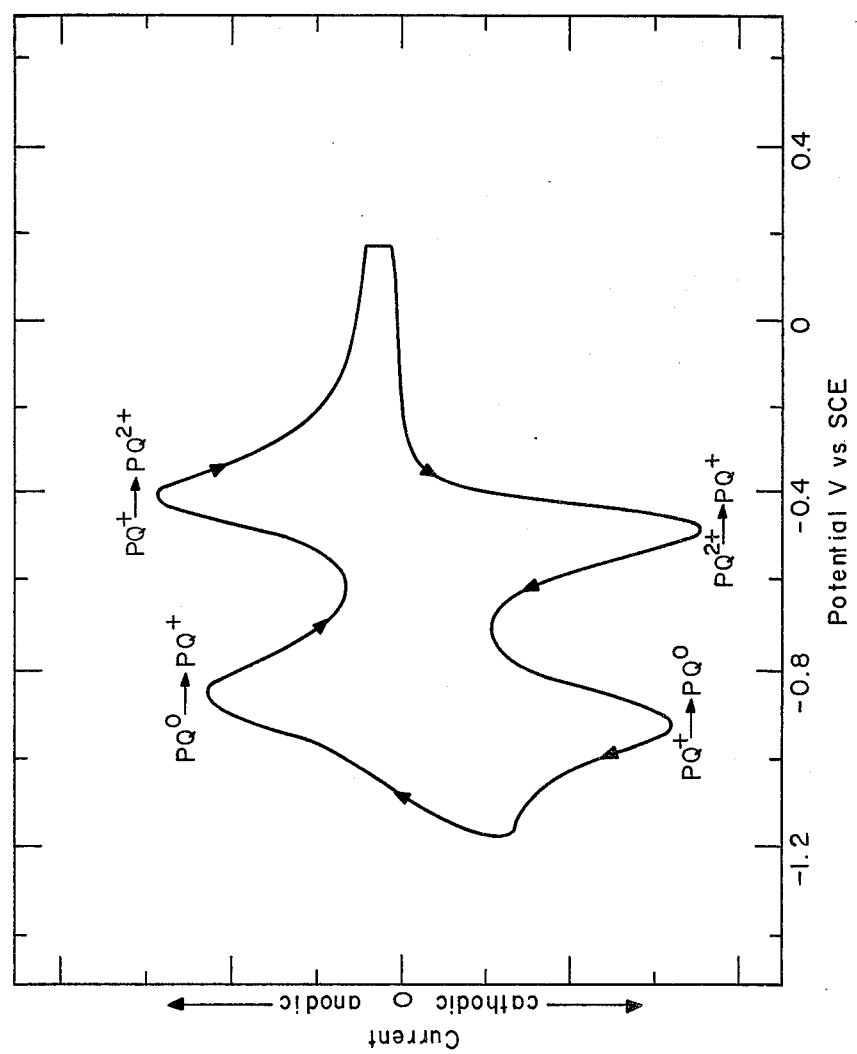
FIG. 1 is a graph of the cyclic voltammetry exhibited by one of our compounds in an electrolyte.

The invention is best described with reference to the following non-limiting examples:

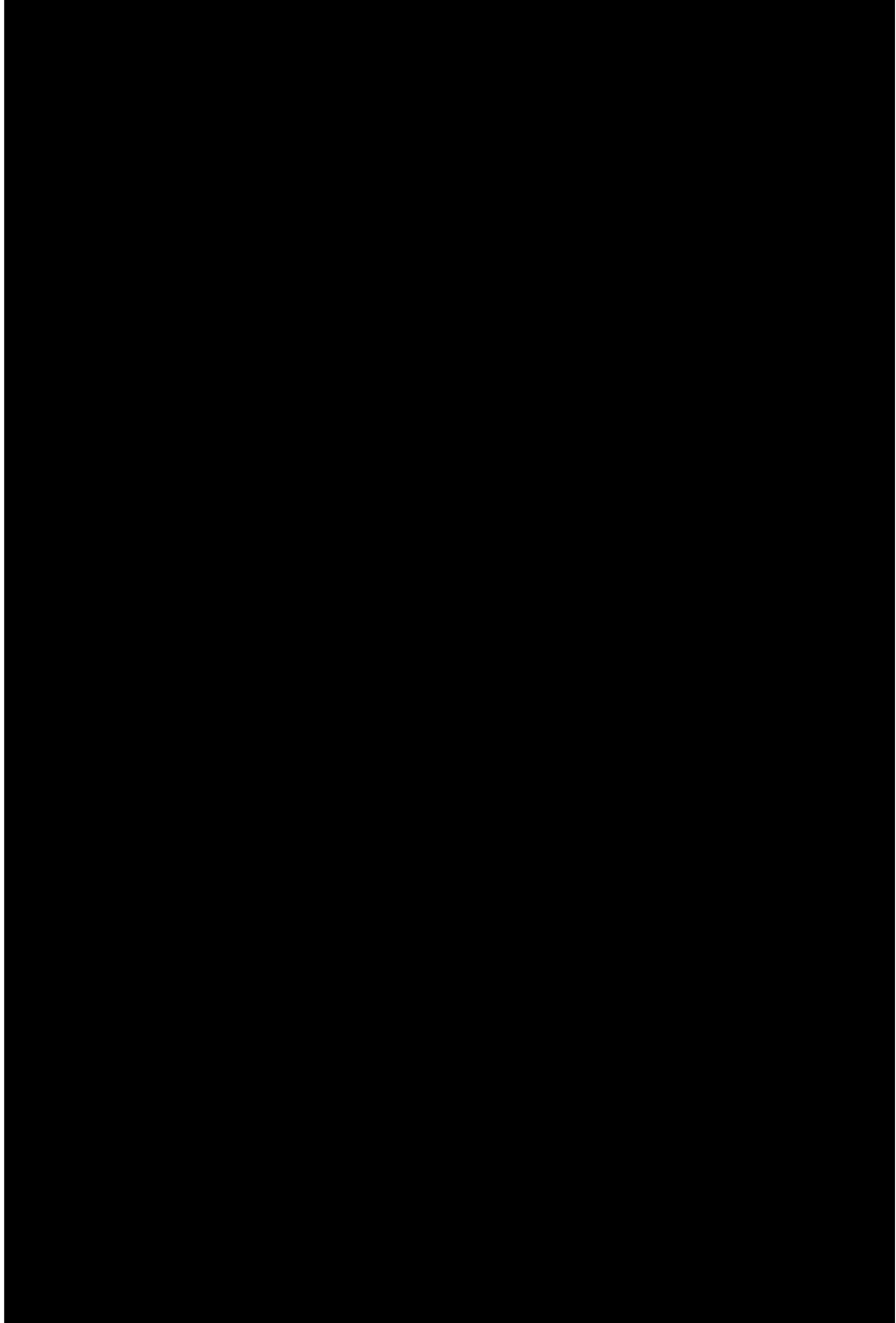

where R is an alkyl group having one to ten carbon atoms or an alkyl-aromatic group having one to ten carbon atoms in an alkyl chain and two or less rings;
where R' is a binding agent choosen from the following group: silicon alkoxides, silicon halogens, boron alkoxides or boron halogens.

and X is a halogen or other anion for charge balance.

9. The salt of claim 8 wherein R is an alkyl group having 3 or less carbon atoms.
10. The salt of claim 8 wherein R' is a silicon alkoxide.
11. The salt of claim 8 wherein X is a bromide.
12. The salt of claim 8 wherein X is a chloride.
13. A salt having the formula:

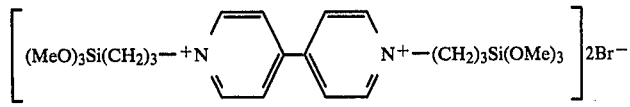

* * * * *